United States Patent
MacKenzie

(10) Patent No.: US 12,226,541 B2
(45) Date of Patent: Feb. 18, 2025

(54) SYSTEM FOR AND METHOD OF ELIMINATING MICROBES WITHIN VEHICLE

(71) Applicant: HYUNDAI MOBIS CO., LTD., Seoul (KR)

(72) Inventor: Douglas C. MacKenzie, Livonia, MI (US)

(73) Assignee: HYUNDAI MOBIS CO., LTD., Seoul (KR)

( * ) Notice: Subject to any disclaimer, the term of this patent is extended or adjusted under 35 U.S.C. 154(b) by 280 days.

(21) Appl. No.: 17/078,025

(22) Filed: Oct. 22, 2020

(65) Prior Publication Data

US 2022/0125975 A1 Apr. 28, 2022

(51) Int. Cl.
*A61L 2/24* (2006.01)
*A61L 2/10* (2006.01)
(Continued)

(52) U.S. Cl.
CPC ........ *A61L 2/24* (2013.01); *A61L 2/10* (2013.01); *A61L 2/202* (2013.01); *B60N 2/0021* (2023.08); *B60N 2/003* (2023.08); *B60Q 9/00* (2013.01); *B60R 25/01* (2013.01); *B60S 1/64* (2013.01); *G08B 21/02* (2013.01); *A61L 2101/02* (2020.08); *A61L 2202/11* (2013.01); (Continued)

(58) Field of Classification Search
CPC ... A61L 2/24; A61L 2/10; A61L 2/202; A61L 2101/02; A61L 2202/11; A61L 2202/13; A61L 2202/14; A61L 2202/25; A61L 2209/111; A61L 2209/212; A61L 9/20; B60N 2/002; B60Q 9/00; B60Q 1/543; B60Q 1/50; B60R 25/01; B60R 16/0234; B60S 1/64; G08B 21/02
See application file for complete search history.

(56) References Cited

U.S. PATENT DOCUMENTS 7,875,173 B1 * 1/2011 Barnes ................ A61H 33/14
4/541.1
8,048,370 B1 * 11/2011 Barnes .................. A61L 9/20
422/4
(Continued)

FOREIGN PATENT DOCUMENTS

CN 101238363 A * 8/2008 ............ A23B 7/015
EP 2119974 A1 * 11/2009 ............ A61L 9/015
(Continued)

OTHER PUBLICATIONS

English translation of KR20190102657 (Year: 2019).*
(Continued)

*Primary Examiner* — Regina M Yoo
(74) *Attorney, Agent, or Firm* — NSIP Law

(57) ABSTRACT

A system for and a method of eliminating a virus within a vehicle. The system includes a sterilizer positioned within a vehicle and configured to eliminate a virus within the vehicle while operating, a detection sensor that detects whether or not an occupant is present within the vehicle, and a sterilization controller that controls operation of the sterilizer with a preset operation profile on the basis of a result of the detection sensor detecting whether or not the occupant is present within the vehicle.

7 Claims, 3 Drawing Sheets

(51) Int. Cl.
*A61L 2/20* (2006.01)
*B60N 2/00* (2006.01)
*B60Q 9/00* (2006.01)
*B60R 25/01* (2013.01)
*B60S 1/64* (2006.01)
*G08B 21/02* (2006.01)
*A61L 101/02* (2006.01)

(52) U.S. Cl.
CPC ....... *A61L 2202/13* (2013.01); *A61L 2202/14* (2013.01); *A61L 2202/25* (2013.01); *B60N 2210/40* (2023.08); *B60N 2230/20* (2023.08)

(56) References Cited

U.S. PATENT DOCUMENTS

| | | | | |
|---|---|---|---|---|
| 10,960,094 | B1* | 3/2021 | Ismail | A61B 1/0016 |
| 2008/0118395 | A1* | 5/2008 | Benedek | A23B 7/144 |
| | | | | 422/123 |
| 2013/0287626 | A1* | 10/2013 | Benedek | A61L 2/202 |
| | | | | 422/2 |
| 2017/0246333 | A1* | 8/2017 | Carbone | A61L 2/202 |
| 2018/0264160 | A1* | 9/2018 | Benedek | A61L 2/10 |
| 2019/0091738 | A1* | 3/2019 | Chen | B60H 1/00742 |
| 2020/0070214 | A1* | 3/2020 | Mangiardi | B08B 3/10 |
| 2021/0322594 | A1* | 10/2021 | Ahmad | A61L 2/10 |
| 2022/0008597 | A1* | 1/2022 | Bergman | A61L 2/24 |
| 2022/0054687 | A1* | 2/2022 | Forzani | A61L 2/22 |
| 2022/0062465 | A1* | 3/2022 | De Francesco | E05B 85/10 |
| 2022/0096684 | A1* | 3/2022 | Trundle | A61L 2/084 |
| 2023/0149583 | A1* | 5/2023 | Aly | G16H 40/20 |
| | | | | 422/105 |

FOREIGN PATENT DOCUMENTS

| | | |
|---|---|---|
| KR | 10-2006-0006702 | 1/2006 |
| KR | 10-0759068 | 9/2007 |
| KR | 10-2010-0010668 | 2/2010 |
| KR | 10-2016-0069827 | 6/2016 |
| KR | 10-2019-0102657 | 9/2019 |

OTHER PUBLICATIONS

English translation of KR1020160069827 (Year: 2016).*
Office Action dated Aug. 29, 2022, issued to Korean Patent Application No. 10-2020-0167456.

* cited by examiner

SYSTEM FOR AND METHOD OF ELIMINATING MICROBES WITHIN VEHICLE

BACKGROUND OF THE INVENTION

Field of the Invention

The present invention relates to a system for and a method of eliminating microbes (e.g., a virus) within a vehicle and, more particularly, to a technology for eliminating microbes within a vehicle with no passengers therein.

Description of the Related Art

Recently, outbreaks of various viruses, including avian influenza viruses and coronaviruses (including COVID-19), have occurred frequently around the world, resulting in people and animals being exposed to infectious diseases. In the event of an infectious disease, various quarantine systems are established, and disinfectants are sprayed in areas where a virus causing the infectious disease is expected to be present. However, it is not easy to completely prevent transmission of the virus that already begins to be spread.

This problem occurs in limited areas, such as a vehicle cabin. Vehicles are fundamentally equipped with an air conditioner for air purification. An internal air conditioning apparatus of the vehicle includes an inlet port, an air circulation motor, an air purification filter, and an internal outlet port. The inlet port through which outside air is introduced is exposed to the outside. The air circulation motor enables the outside air to flow through the inlet port. The air purification filter filters out dust or the like from the introduced outside air. The outside air that passes through the air purification filter is discharged into an internal space in the vehicle. The air purification filter filters out a contaminant having the same size as or a greater size than fine dust but does not filter out microorganisms, viruses, or the like.

Particularly, in the case of using a vehicle sharing service, a robotaxi service (i.e., an autonomous driverless taxi service), or the like, a new passenger can be infected with viruses or microorganisms that are spread into the vehicle from previous passengers.

The foregoing is intended merely to aid in understanding the background of the present invention and therefore should not be interpreted to admit that the present invention falls within the purview of the related art that is already known to a person of ordinary skill in the art.

An example of the related art is Korean Patent Application Publication No. KR 10-2010-0010668.

SUMMARY OF THE INVENTION

An object of the present invention is to provide a system for and a method of eliminating viruses within a vehicle with no occupants being present within the vehicle.

According to an aspect of the present invention, there is provided a system for eliminating a virus within a vehicle, the system including: a sterilizer positioned within a vehicle and configured to eliminate a virus within the vehicle while operating; a detection sensor that detects whether or not an occupant is present within the vehicle; and a sterilization controller that controls operation of the sterilizer with a preset operation profile on the basis of a result of the detection sensor.

In the system, the sterilizer may be an ultraviolet light generator that emits UV-C light into the vehicle.

In the system, the sterilizer may be an ozone generator that generates ozone gas and introduces the generated ozone gas into the vehicle.

In the system, the sterilizer may include an ultraviolet light generator that emits UV-C light into the vehicle and an ozone generator that generates ozone gas and introduces the generated ozone gas into the vehicle, and the sterilization controller may sequentially enable the ozone generator and the ultraviolet light generator to operate, and thus the ozone gas within the vehicle may be eliminated with the UV-C light.

The system may further include an ozone sensor that detects a concentration of ozone gas within the vehicle; and a vehicle controller that determines an operating state of the sterilizer on the basis of the concentration of ozone gas, detected by the ozone sensor.

In the system, the sterilizer may include an ultraviolet light generator that emits UV-C light into the vehicle, and an ozone generator that generates ozone gas and introduces the generated ozone gas into the vehicle, and the sterilization controller may selectively enable any one of the ozone generator and the ultraviolet light generator to operate, depending on a condition for operating the sterilizer.

The system may further include a locking device that enables or disables opening of a door of the vehicle, and a vehicle controller that, while the sterilizer operates, controls the locking device to disable the opening of the door of the vehicle.

The system may further include a door sensor that detects whether or not a door of the vehicle is opened, and a vehicle controller that controls the sterilization controller to interrupt operation of the sterilizer, when the door sensor detects that the door of the vehicle is opened.

The system may further include a door sensor that detects whether or not a door of the vehicle is opened; and a vehicle controller that provides a health warning to the occupant inside the vehicle or to the outside when the door sensor detects that the door of the vehicle is opened.

The system may further include a vehicle controller that indicates an operating state of the sterilizer to the outside or transmits operating data thereof to the outside.

According to another aspect of the present invention, there is provided a method of eliminating a virus within a vehicle, the method including: determining whether or not an elimination condition for eliminating a virus spread into a vehicle is satisfied; detecting whether or not an occupant is present within the vehicle, when the elimination condition is satisfied; and controlling operation of a sterilizer sterilizing the virus spread into the vehicle, with a preset operation profile, on the basis of a result of the detection of whether or not the occupant is present within the vehicle.

In the method, in the controlling of the operation of the sterilizer, an ultraviolet light generator emitting UV-C light into the vehicle may be enabled to operate.

In the method, in the controlling of the operation of the sterilizer, ozone gas may be generated and the generated ozone gas may be introduced into the vehicle.

In the method, the controlling of the operation of the sterilizer may include generating ozone gas and introducing the generated ozone gas into the vehicle, and enabling an ultraviolet light generator emitting UV-C light into the vehicle to operate and thus eliminating ozone gas.

The method may further include detecting a concentration of ozone gas within the vehicle, and determining an operating state of the sterilizer on the basis of the concentration of ozone, detected by an ozone sensor, in which the detecting of the concentration of ozone gas and the determining of the operating state of the sterilizer may be performed after the controlling of the operation of the sterilizer.

In the method, in the controlling of the operation of the sterilizer, depending on a condition for operating the sterilizer, an ultraviolet light generator emitting UV-C light into the vehicle may be selectively enabled to operate, or ozone gas may be generated and the generated ozone gas may be introduced into the vehicle.

In the method, in the controlling of the operation of the sterilizer, while the sterilizer operates, a locking device may be controlled to disable opening of a door of the vehicle.

In the method, in the controlling of the operation of the sterilizer, when a door sensor detects that a door of the vehicle is opened, the operation of the sterilizer may be interrupted.

In the method, in the controlling of the operation of the sterilizer, when a door sensor detects that a door of the vehicle is opened, a health warning may be provided to the occupant inside the vehicle or to the outside.

The method may further include indicating an operating state of the sterilizer to the outside or transmitting operating data thereof to the outside, in which the indicating of the operating state or the transmitting of the operating data may be performed after the controlling of the operation of the sterilizer.

According to the present invention, a virus that is spread into a vehicle by an occupant can be eliminated.

In addition, since a sterilizer operates with no occupants being present within a vehicle, human health is not endangered by the sterilizer.

DETAILED DESCRIPTION OF THE INVENTION

Figure 1:
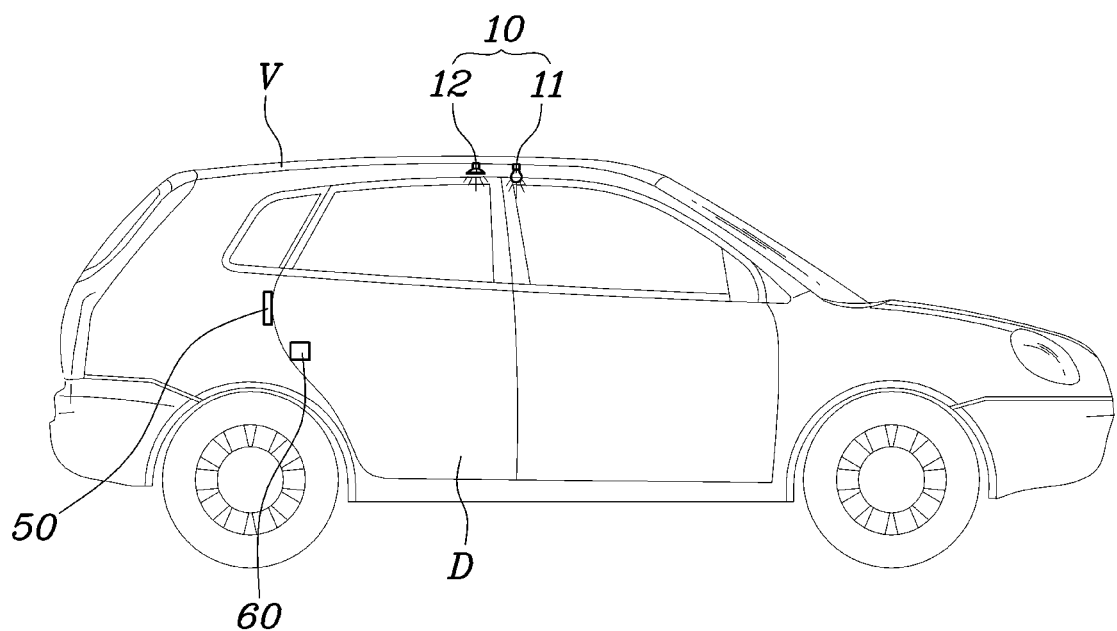
FIG. 1 is a diagram illustrating a vehicle equipped with a virus elimination system according to an embodiment of the present invention.

For illustrative purpose only, embodiments of the present invention disclosed herein will be described in terms of specific structures and functions. The embodiments of the present invention may be implemented in various ways and therefore should not be construed as limiting the present invention.

Various modifications may be made in various ways to the embodiments of the present invention. Among these, specific embodiments will be described in detail below with reference to the accompanying drawings. However, this description does not limit the embodiments of the present invention to the disclosed specific embodiments. All alterations, equivalents, and substitutes that are included within the technical idea of the present invention should be understood as falling within the scope of the present invention.

The terms first, second, and so on may be used to describe various constituent elements but should not limit these constituent elements. These terms are only used to distinguish one constituent element from another. For instance, a first constituent element may be termed a second constituent element without departing from the scope of each claim that defines the present invention. Likewise, the second constituent element may also be termed the first constituent element.

It should be understood that, when a constituent element is referred to as being "coupled to" or "connected to" a different constituent element, the constituent element may be coupled to or connected to the different constituent element, or an intervening constituent element may also be present therebetween. In contrast, it should be understood that, when a constituent element is referred to as being "directly coupled to" or "directly connected to" a different constituent element, no intervening constituent element is present therebetween. Expressions describing a relationship between constituent elements, such as "between" and "directly between", and "adjacent to" and "directly adjacent to", should be construed in the same manner.

The terms used herein are only for describing specific embodiments and are not intended to limit the present invention. A noun in the singular is construed as that in the plural, except as distinctively expressed in context. It should be understood that, throughout the present specification, the term "include", "have", or the like is intended to indicate that a feature, a number, a step, an operation, a constituent element, a component, or any combination thereof is present, without precluding the presence or addition of one or more other features, numbers, steps, operations, constituent elements, or any combination thereof.

Unless otherwise defined, each of all terms used herein, including technical or scientific terms, has the same meaning as is normally understood by a person of ordinary skill in the art to which the present invention pertains. The term as defined in commonly used dictionaries should be construed as having the same meaning in context as that in the related art and, unless otherwise explicitly defined in the present specification, should not be construed as having an excessively implied meaning or a purely literal meaning.

Preferable embodiments of the present invention will be described in detail below with reference to the accompanying drawings. The same reference numbers refer to the same constituent elements throughout the drawings.

Figure 2:
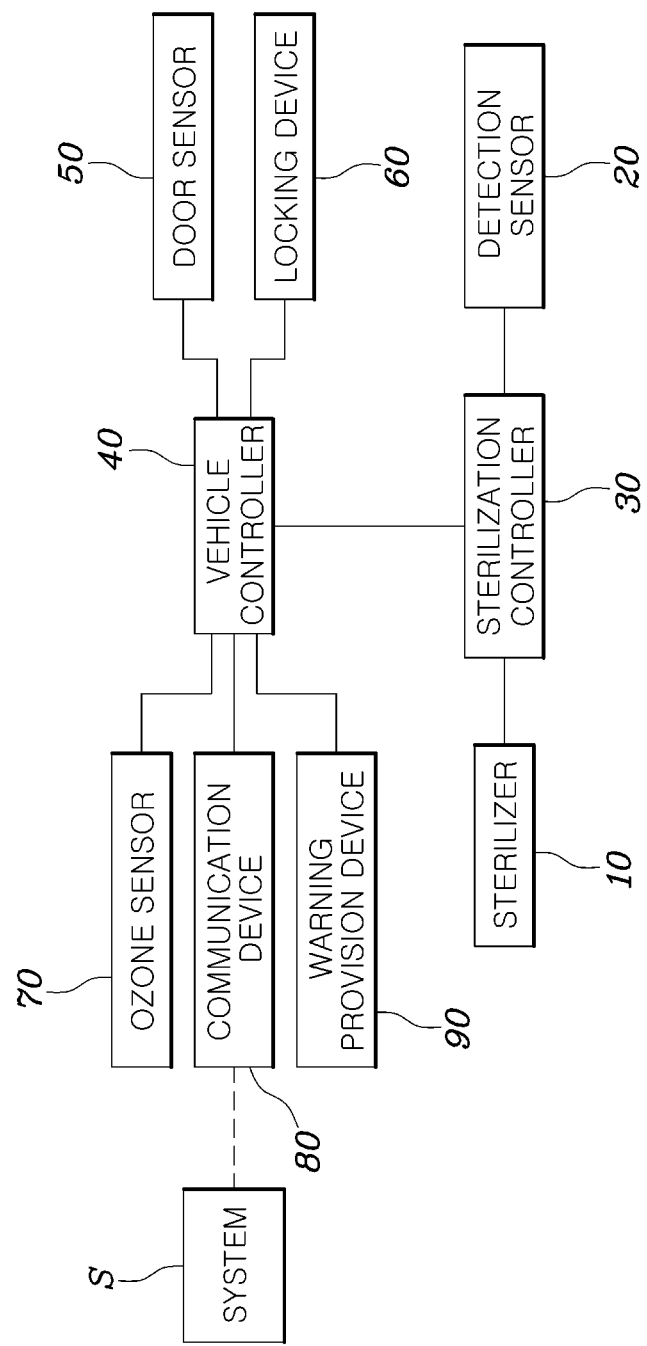
FIG. 2 is a diagram illustrating the construction of the virus elimination system according to the embodiment of the present invention.

FIG. 1 illustrates a vehicle equipped with a system for eliminating a virus within a vehicle according to an embodiment of the present invention. FIG. 2 illustrates a configuration of the system for eliminating a virus within a vehicle according to the embodiment of the present invention.

With reference to FIGS. 1 and 2, the system for eliminating a virus within a vehicle according to the embodiment of the present invention includes a sterilizer 10, a detection sensor 20, and a sterilization controller 30. The sterilizer 10 is positioned within a vehicle and eliminates a virus while the sterilizer 10 operates. The detection sensor 20 detects whether or not an occupant is present within the vehicle. The sterilization controller 30 controls operation of the sterilizer 10 with a preset operation profile on the basis of a result of the detection sensor 20 detecting whether or not the occupant is present within the vehicle.

The sterilizer 10 may be a device that eliminates a microbe that is spread into the vehicle or be a device that eliminates particularly a virus that is spread in the vehicle. The elimination here of the virus includes all preventive actions for making it impossible for the virus to integrate into a host, such as destroying or deactivating the virus.

The detection sensor 20 detects whether or not the occupant is present within the vehicle. Occupants here include a human, a family pet, and a domestic or tamed animal.

The detection sensor 20, for example, may be a pressure sensor installed in a seat, a camera sensor that photographs the inside of the vehicle, or a thermal detection sensor 20.

Furthermore, the detection sensor 20 may be a gas detection sensor 20 that detects a concentration of carbon dioxide. The detection sensor 20 detects a change in the concentration of carbon dioxide within the vehicle and thus detects whether or not an occupant is present.

In a case where the detection sensor 20 detects that an occupant is not present, the sterilization controller 30 controls the operation of the sterilizer 10 with the preset operation profile.

The present operation profile here includes the time, the sterilization level, and the like for the operation of the sterilizer 10, such as an ultraviolet light generator 11 or an ozone generator 12 that will be described below.

Particularly, the preset operation profile may be changed depending on an elimination condition that will be described below. According to an embodiment, the preset operation profile may be changed according to the number of occupants in the vehicle, the time for which the occupant is present within the vehicle, and the like.

The sterilization controller 30 according to the embodiment of the present invention is realized by a nonvolatile memory (not illustrated) and a processor (not illustrated). The nonvolatile memory stores data associated with an algorithm developed to control operation of each of various components of the vehicle or with a software command for executing the algorithm. The processor performs a below-described operation using the data stored in the memory. The memory and processor described here are realized as individual chips. Alternatively, the memory and processor may be realized as a single integrated chip. The processor may include one or more processors.

Additionally, a vehicle controller 40 determines whether or not an elimination condition for eliminating a virus spread into a vehicle is satisfied.

According to an embodiment, the elimination condition may be that an occupant should be present within a vehicle for a preset time or longer and then should get off the vehicle. The vehicle here may be a driverless vehicle, such as a robotaxi. In this case, when an occupant gets off the vehicle and a door is closed, the elimination condition is satisfied.

The sterilizer 10 may be an ultraviolet light generator 11 emitting UV-C light into the vehicle. The ultraviolet light generator 11 may be an ultraviolet light lamp that generates ultraviolet light and emits the generated ultraviolet light into the vehicle.

The UV-C light has a wavelength of 100 nm to 280 nm and is known to be particularly effective in eliminating a virus.

The sterilizer 10 may be an ozone generator 12 that generates ozone gas and introduces the generated ozone gas into the vehicle.

The ozone generator 12, mounted inside the vehicle, independently generates ozone gas inside the vehicle or supplies ozone gas generated outside the vehicle into the vehicle.

When ozone decomposes to molecular oxygen, this molecular oxygen reacts with another substance for its oxidation. A bacterium, a microbe, or a virus is eliminated using this property of ozone.

According to an embodiment, the sterilization controller 30 sequentially enables the ozone generator 12 and the ultraviolet light generator 11 to operate. Thus, the ozone gas within the vehicle is eliminated with the ultralight light.

The sterilization controller 30 first enables the ozone generator 12 to operate to introduce ozone gas into the vehicle. After a preset operating time has elapsed, the sterilization controller 30 enables the ultraviolet light generator 11 to operate.

The ultraviolet light generator 11 emits ultraviolet light into the vehicle, and thus the ozone gas introduced into the vehicle decomposes into oxygen. Accordingly, the ozone gas is eliminated without being discharged out of the vehicle.

According to another embodiment, an air conditioning system in the vehicle is enabled to operate in a mode in which outdoor air flows into and out of the vehicle, and thus the ozone gas within the vehicle is eliminated.

The system for eliminating a virus within a vehicle may further include an ozone sensor 70 and a vehicle controller 40. The ozone sensor 70 detects a concentration of ozone within the vehicle. The vehicle controller 40 determines an operating state of the sterilizer 10 on the basis of the concentration of ozone, detected by the ozone sensor 70.

The ozone sensor 70 detects the concentration of ozone gas in inside air within the vehicle. When the concentration of ozone gas is equal to or lower than a preset concentration X, the vehicle controller 40 determines that the operation of the sterilizer 10 is completed. Conversely, when the concentration of zone is higher than the preset concentration X, the vehicle controller 40 determines that the operation of the sterilizer 10 is not completed and that a state of being harmful to a human body is thus maintained.

According to another embodiment, the sterilization controller 30 selectively activates any one of the ozone generator 12 and the ultraviolet light generator 11, depending on a condition for operating the sterilizer 10.

The condition here for operating the sterilizer 10 is any one of the following: malfunctioning of one or both of the ozone generator 12 and the ultraviolet light generator 11, limiting of the time for sterilization, and satisfying of the above-described elimination condition for eliminating a virus.

According to an embodiment, in a case where the time for sterilization is limited, the ultraviolet light generator 11 is enabled to operate. Conversely, in a case where the time for sterilization is equal to or longer than a preset time limit, the ozone generator 12 is enabled to operate.

The system for eliminating a virus within a vehicle may further include a locking device 60 and a vehicle controller 40. The locking device 60 enables or disables opening of a door of the vehicle. While the sterilizer 10 operates, the vehicle controller 40 controls the locking device 60 to disable the opening of the door of the vehicle.

The locking device 60 is a device that is controlled by the vehicle controller 40 and operates to enable or disable the opening of the door of the vehicle. In a state where the sterilizer 10 operates, the vehicle controller 40 controls the locking device 60 to disable the opening of the door of the vehicle.

In order to eliminate a virus, the sterilizer 10 generates ultraviolet light, ozone gas, or the like that has the likelihood of having a harmful effect on the human body. Therefore, in a state where the sterilizer 10 operates, the opening of the door of the vehicle is disabled to prevent a person from entering the vehicle.

The system for eliminating a virus within a vehicle may further include a door sensor 50 and a vehicle controller 40. The door sensor 50 detects whether or not the door of the vehicle is opened. When the door sensor 50 detects that the door of the vehicle is opened, the vehicle controller 40 controls the sterilization controller 30 to interrupt the operation of the sterilizer 10.

Although controlled by the locking device 60, the door sensor 50 detects whether or not the door of the vehicle is opened. When the door sensor 50 detects that the door of the vehicle is opened, the vehicle controller 40 controls the sterilization controller 30 to immediately interrupt the operation of the sterilizer 10.

Additionally, when the door sensor 50 detects that the door of the vehicle is opened, the vehicle controller 40 provides a health warning to the occupant inside the vehicle or to the outside.

Specifically, the vehicle controller 40 is connected to a warning provision device 90. While the sterilizer 10 operates, when it is detected that the door of the vehicle is opened, the vehicle controller 40 controls the warning provision device 90 to provide the health warning to the occupant inside the vehicle or to the outside.

According to an embodiment, the warning provision device 90 may be a lamp, a horn, a speaker, or the like that is installed in the vehicle. The warning provision device 90 provides a visual health warning, an audio health warning, or the like to the occupant inside the vehicle or to the outside.

The system for eliminating a virus within a vehicle may further include a vehicle controller 40 that indicates an operating state of the sterilizer 10 to the outside or transmits operating data thereof to the outside.

Specifically, the vehicle controller 40 is connected to the warning provision device 90 and controls the warning provision device 90 to indicate the operating state of the sterilizer 10 to the outside. Alternatively, the vehicle controller 40 is connected to a communication device 80 and controls the communication device 80 to transmit the operating data to the outside.

According to an embodiment, the warning provision device 90 may be a lamp attached to the outside of the vehicle. The operation state of the sterilizer 10 is indicated by changing a color of light emitted from the lamp.

According to an embodiment, the communication device 80 may be a device that wirelessly communicates with a remote vehicle control system S. Particularly, the operating data of the sterilizer 10 is transmitted to the remote vehicle control system S.

According to an embodiment, the vehicle may be an autonomous vehicle that is controlled by the remote vehicle control system S. The remote vehicle control system S may be a service platform that provides an autonomous taxi service. In a case where it is determined on the basis of the received operating data of the sterilizer 10 that the operating state of the sterilizer 10 is a completely sterilized state, the remote control system S performs matching to a new occupant (customer).

Figure 3:
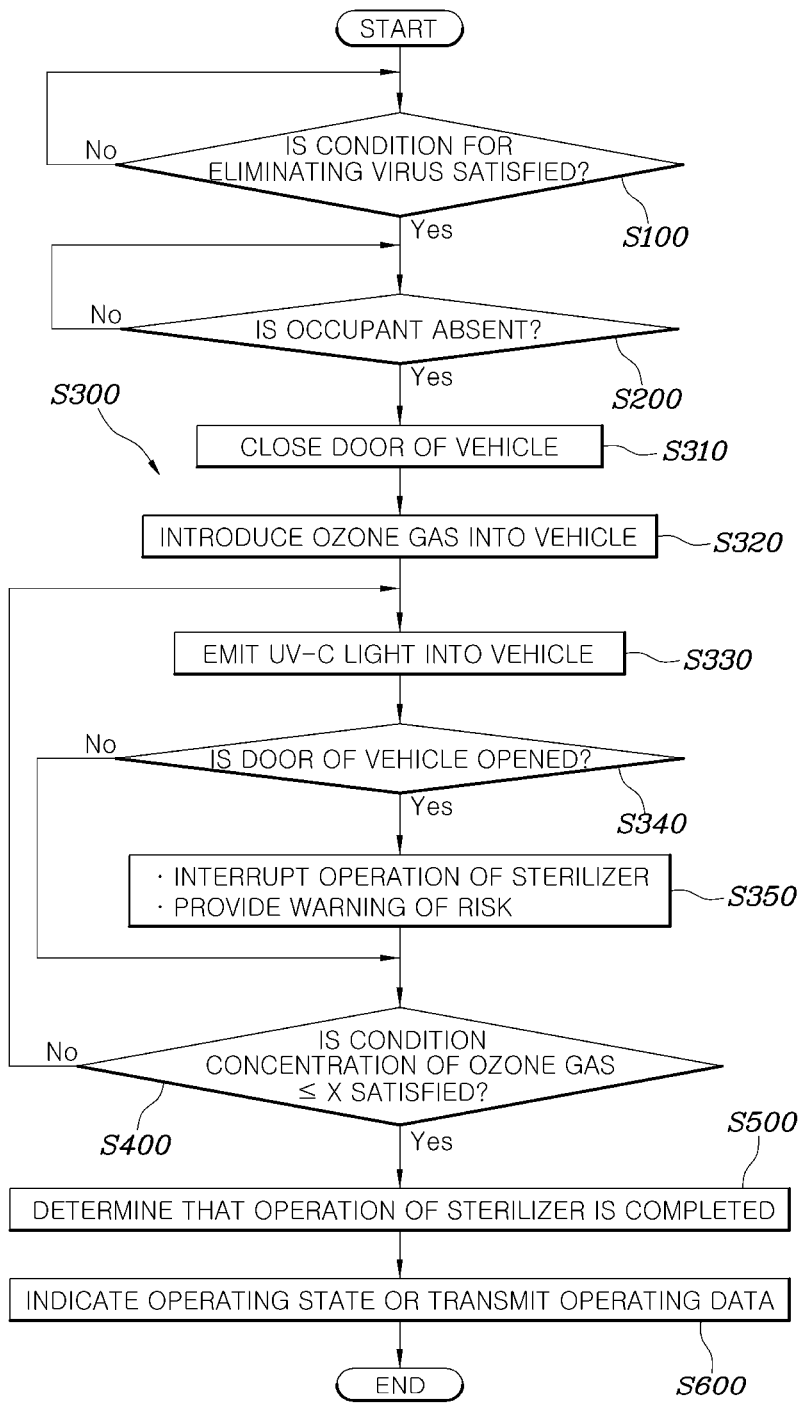
FIG. 3 is a flowchart illustrating a virus elimination method according to an embodiment of the present invention.

FIG. 3 is a flowchart illustrating a method of eliminating a virus within a vehicle according to an embodiment of the present invention.

With reference to FIG. 3, the method of eliminating a virus within a vehicle according to the embodiment of the present invention includes Step S100 of determining whether or not an elimination condition for eliminating a virus spread into a vehicle is satisfied, Step S200 of detecting whether or not an occupant is present within the vehicle, when the elimination condition is satisfied, and Step S300 of controlling operation of a sterilizer eliminating the virus spread within the vehicle, with a preset operation profile, on the basis of a result of the detection of whether or not the occupant is present within the vehicle.

In Step S300 of controlling operation of a sterilizer, an ultraviolet light generator emitting UV-C light into the vehicle may be enabled to operate (S330).

In Step S300 of controlling operation of a sterilizer, ozone gas may be generated and the generated ozone gas is introduced into the vehicle (S320).

Step S300 of controlling operation of a sterilizer may include Step S320 of generating ozone gas and introducing the generated ozone gas into the vehicle, and Step S330 of enabling an ultraviolet light generator emitting the UV-C light into the vehicle to operate and thus eliminating the zone gas.

The method of eliminating a virus within a vehicle may further include Step S400 of detecting a concentration of ozone gas within the vehicle, and Step S500 of determining an operating state of the sterilizer on the basis of the concentration of ozone, detected by an ozone sensor. Step S400 and Step S500 are performed subsequently to Step S300 of controlling operation of a sterilizer.

In Step S300 of controlling operation of a sterilizer, depending on a condition for operating the sterilizer, the ultraviolet light generator emitting the UV-C light into the vehicle may be selectively generated (S330), or ozone gas may be generated and the generated ozone gas may be introduced into the vehicle (S320).

Particularly, Step S300 of controlling operation of a sterilizer may include Step S310 of closing a door of the vehicle before introducing the ozone gas (S320) or before emitting the UV-C light (S330).

In Step S300 of controlling operation of a sterilizer, while the sterilizer operates, a locking device may be controlled to disable opening of the door of the vehicle (S310).

In Step S300 of controlling operation of a sterilizer, when a door sensor detects that the door of the vehicle is opened, the operation of the sterilizer may be interrupted (S350).

In Step S300 of controlling operation of a sterilizer, when the door sensor detects that the door of the vehicle is opened, a health warning may be provided to the occupant inside the vehicle or to the outside (S350).

The method of eliminating a virus within a vehicle may further include Step S600 of indicating an operating state of the sterilizer to the outside or transmitting operating data thereof to the outside. Step S600 is performed subsequently to Step S300 of controlling operation of the sterilizer.

The specific embodiments of the present invention are illustrated and described, and it would be obvious to a person of ordinary skill in the art that various modifications and alterations are possibly made to the present invention without departing from the technical idea of the present invention that is claimed in the following claims.

What is claimed is:

1. A system for eliminating microbes within a vehicle, the system comprising:
   a sterilizer positioned within the vehicle to eliminate microbes within the vehicle when the sterilizer operates;
   a detection sensor that detects whether or not an occupant is present within the vehicle;
   a sterilization controller configured to control an operation of the sterilizer according to a preset operation profile, depending on whether or not the occupant is present within the vehicle;
   a locking device that enables or disables opening of a door of the vehicle;

a door sensor that detects whether or not a door of the vehicle is opened; and a vehicle controller, wherein the vehicle controller is connected to a warning device and a communication device, and configured to:

control the warning device to indicate an operating state of the sterilizer that is observable outside of the vehicle; and control the communication device to transmit operating data corresponding to the operating state of the sterilizer outside of the vehicle, and wherein the vehicle controller is connected to the sterilizer and the locking device, and further configured to:

control the locking device to disable the opening of the door of the vehicle while the sterilizer is in operation; and control the warning device to provide a health warning to the occupant inside the vehicle, or a health warning that is observable outside of the vehicle in response to a detection by the door sensor that the door of the vehicle is opened.

2. The system according to claim 1, wherein the sterilizer is comprises an ultraviolet light generator that emits UV-C light within the vehicle.

3. The system according to claim 1, wherein the sterilizer is comprises an ozone generator configured to generate ozone gas and introduce the generated ozone gas within the vehicle.

4. The system according to claim 1, wherein the sterilizer comprises:

an ultraviolet light generator that emits UV-C light within the vehicle; and an ozone generator that generates ozone gas and introduces the generated ozone gas within the vehicle, and wherein the sterilization controller is further configured to sequentially enable an operation of the ozone generator, followed by an operation of the ultraviolet light generator, such that the ozone gas inside the vehicle is eliminated by the UV-C light.

5. The system according to claim 4, further comprising:

an ozone sensor that detects a concentration of the ozone gas that is present inside the vehicle, wherein the vehicle controller is further configured to determine an operating state of the sterilizer based on the concentration of ozone gas, detected by the ozone sensor.

6. The system according to claim 1, wherein the sterilizer comprises:

an ultraviolet light generator that emits UV-C light into the vehicle; and an ozone generator that generates ozone gas and introduces the generated ozone gas into the vehicle, and wherein the sterilization controller is further configured to selectively enable any one of the ozone generator and the ultraviolet light generator to operate, depending on a condition for operating the sterilizer.

7. The system according to claim 1, wherein the vehicle controller is further configured to control the sterilization controller to interrupt operation thereof, in response to a detection by the door sensor that the door of the vehicle is opened.

* * * * *